(12) United States Patent
Ankerson

(10) Patent No.: US 7,994,329 B2
(45) Date of Patent: *Aug. 9, 2011

(54) GROWTH HORMONE SECRETAGOGUE RECEPTOR TYPE 1A AGONISTS

(75) Inventor: Michael Ankerson, Belle Mead, NJ (US)

(73) Assignee: Helsinn Therapeutics (U.S.), Inc., Bridgewater, NJ (US)

( * ) Notice: Subject to any disclaimer, the term of this patent is extended or adjusted under 35 U.S.C. 154(b) by 36 days.

This patent is subject to a terminal disclaimer.

(21) Appl. No.: 11/424,885

(22) Filed: Jun. 19, 2006

(65) Prior Publication Data

US 2007/0066540 A1    Mar. 22, 2007

Related U.S. Application Data

(63) Continuation of application No. 11/150,736, filed on Jun. 10, 2005, now abandoned, which is a continuation of application No. 10/649,386, filed on Aug. 27, 2003, now abandoned, which is a continuation of application No. 09/771,770, filed on Jan. 29, 2001, now abandoned.

(60) Provisional application No. 60/181,303, filed on Feb. 9, 2000.

(51) Int. Cl.
*C07D 211/18*    (2006.01)
*A61K 31/4535*    (2006.01)

(52) U.S. Cl. ...... 546/232; 546/333; 514/207; 514/232.2
(58) Field of Classification Search ............... 514/232.2, 514/333; 546/207, 232
See application file for complete search history.

(56) References Cited

U.S. PATENT DOCUMENTS 6,566,337 B1 * 5/2003 Ankersen et al. ............... 514/19

FOREIGN PATENT DOCUMENTS

| WO | WO 9723508 | * | 7/1997 |
| WO | WO 9958501 | * | 11/1999 |

OTHER PUBLICATIONS

Kenmei Okada et al , 1996 Intracerebroventricular Administration of the Growth Hormone-Releasing peptide KP-102 increases food intake in free feeding rats.*
Locke et al Intracerebroventricular growth-hormone-releasing peptide-6 stimulates eating without affecting plasma growth hormone responses in rates 1995.*
Scacchi et al , 1997, Spontaneous Nocturanal secretion of Growth Hormone in Anorexia Nervosa.*

* cited by examiner

*Primary Examiner* — Rita Desai
(74) *Attorney, Agent, or Firm* — Arnall Golden Gregory LLP; Clark G. Sullivan

(57) ABSTRACT

Compounds that are ligands for the growth hormone secretagogue receptor type 1A (GHS-R 1A), as well as pharmaceutically acceptable salts of such compounds, are useful for the manufacture of medicaments for the regulation of food intake.

2 Claims, No Drawings

GROWTH HORMONE SECRETAGOGUE RECEPTOR TYPE 1A AGONISTS

CROSS-REFERENCE TO RELATED PATENT APPLICATIONS

This patent application is a continuation of U.S. patent application Ser. No. 11/150,736, filed Jun. 10, 2005, now abandoned which is a continuation of U.S. patent application Ser. No. 10/649,386, filed Aug. 27, 2003, now abandoned which is a continuation of U.S. patent application Ser. No. 09/771,770, filed Jan. 29, 2001, now abandoned and claims the benefit of U.S. Provisional Patent Application 60/181,303, filed Feb. 9, 2000, and Danish Patent Applications PA 2000 00161 and PA 2000 01107 filed Feb. 1, 2000 and Jul. 17, 2000, respectively, the entire content of each of which is hereby incorporated by reference.

FIELD OF THE INVENTION

This invention relates to the use of a compound that is a ligand for, and acts as an agonist of, the growth hormone secretagogue receptor type 1A (GHS-R 1A), for the regulation of food intake or food intake. The present invention also embraces pharmaceutical compositions comprising these compounds and methods of using the compounds and their pharmaceutical compositions.

BACKGROUND OF THE INVENTION

Stimulation of food intake is important in connection with patients suffering from anorexia due to chronic medical conditions, eating disorders, and other conditions in which excessive weight loss has produced a detrimental effect on the patients' health.

SUMMARY OF THE INVENTION

The present invention relates, inter alia, to the use of a compound that is an agonist for the receptor GHS-R 1A, or pharmaceutically acceptable salts thereof, for the manufacture of a medicament for the regulation of food intake.

DESCRIPTION OF THE INVENTION

Accordingly, the present invention provides the use of a compound that is an agonist for the receptor GHS-R 1A, or pharmaceutically acceptable salts thereof, for the manufacture of a medicament for the regulation of food intake.

A further aspect of the present invention relates to a method for the regulation of food intake, which method comprises administering an effective amount of a compound that is an agonist for the receptor GHS-R 1A, or pharmaceutically acceptable salts thereof, to a patient in need of such a treatment.

A still further aspect of the present invention relates to the use of a compound that is an agonist for the receptor GHS-R 1A, or pharmaceutically acceptable salts thereof, for the manufacture of a medicament for the regulation of Body Mass Index (BMI).

A further aspect of the present invention relates to the use of a compound that is an agonist for the receptor GHS-R 1A, or pharmaceutically acceptable salts thereof, for the manufacture of a medicament for the treatment of anorexia.

A still further aspect of the present invention relates to the use of a compound that is an agonist for the receptor GHS-R 1A, or pharmaceutically acceptable salts thereof, for the manufacture of a medicament for the treatment of lack of appetite in children with a growth hormone deficiency.

A still further aspect of the present invention relates to the use of a compound that is an agonist for the receptor GHS-R 1A, or pharmaceutically acceptable salts thereof, for the manufacture of a medicament for the treatment of Type II diabetes.

A further aspect of the present invention relates to the use of a compound that is an agonist for the receptor GHS-R 1A, or pharmaceutically acceptable salts thereof, for the manufacture of a medicament for the treatment of wasting associated with various diseases or conditions, e.g., wasting associated with AIDS, chronic liver disease, chronic obstructive pulmonary disease (COPD) or respiratory insufficiency in general, as well as wasting associated with bone fractures or with ageing. Wasting, which involves a progressive loss of body mass, including muscle mass, is normally attributable to a catabolic state of metabolism, and is frequently difficult to reverse by purely dietary means.

In one embodiment of the present invention the receptor GHS-R 1A is the human GHS-R 1A receptor. In another embodiment the medicament is for humans.

In a still further embodiment of the invention the compound does not induce a therapeutically effective growth hormone release at the therapeutic dose of the compound.

In a further embodiment of the invention the medicament is a non-injectable medicament. In a still further embodiment the medicament is an oral medicament.

The receptor GHS-R 1A (the growth hormone secretagogue receptor type 1A) is described by Howard, A. D. et al. (1996) in Science 273, 974-977.

The binding of a compound to the receptor GHS-R 1A can, e.g., be measured by the use of the assays as described in Example 1 herein.

In one embodiment of the invention the ligand has a potency ($EC_{50}$) on the GHS-R 1A of less than 500 nM. In another embodiment the ligand has a potency ($EC_{50}$) on the GHS-R 1A of less than 100 nM.

In a further embodiment the binding constant ($K_D$) of the ligand is less than 500 nM. In a still further embodiment the binding constant ($K_D$) of the ligand is less than 100 nM.

In yet another embodiment of the invention the ligand is an agonist for the receptor GHS-R 1A.

In a still further embodiment the compound employed in accordance with the invention is adenosine. In a further embodiment the compound is ghrelin or a peptide homologous thereto. Ghrelin is described by Kojima in Nature (1999), vol. 402, 656-660.

Peptides homologous to ghrelin are peptides which have an amino acid sequence which has a degree of identity to ghrelin of at least about 70%, preferably at least about 80%, more preferably at least about 90%, even more preferably at least about 95%, and most preferably at least about 97%, and which qualitatively retain the activity as a ligand for the receptor GHS-R 1A. The degree of identity between two or more amino acid sequences may be determined by means of computer programs known in the art, such as GAP provided in the GCG program package (Needleman and Wunsch, 1970, Journal of Molecular Biology 48:443-453). For the purposes of determining the degree of identity between two amino acid sequences for the present invention, GAP is used with the following settings: GAP creation penalty of 3.0 and GAP extension penalty of 0.1.

Within the context of the present invention, "a therapeutically effective growth hormone release" is to be understood as a growth hormone release that would have a therapeutic effect in treatment of the specific indication, e.g., regulation of food intake.

The therapeutic dose of the compound will depend upon the frequency and mode of administration, the sex, age, weight and general condition of the subject treated, the nature and severity of the condition treated and any concomitant diseases to be treated, and other factors evident to those skilled in the art. In one embodiment, the effective amount of the compound is in the range from about 0.05 to about 2000 mg, preferably from about 0.1 mg to about 1000 mg, and especially from about 0.5 to about 500 mg per day.

The present invention also encompasses pharmaceutically acceptable salts of the present compounds. Such salts include pharmaceutically acceptable acid addition salts, pharmaceutically acceptable metal salts, ammonium salts and alkylated ammonium salts. Acid addition salts include salts of inorganic acids as well as organic acids. Representative examples of suitable inorganic acids include hydrochloric, hydrobromic, hydriodic, phosphoric, sulfuric and nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, ethylenediaminetetraacetic (EDTA), p-aminobenzoic, glutamic, benzenesulfonic and p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium and magnesium salts and the like. Examples of ammonium and alkylated ammonium salts include ammonium, methylammonium, dimethylammonium, trimethylammonium, ethylammonium, hydroxyethylammonium, diethylammonium, butylammonium and tetramethylammonium salts and the like.

Also included within the scope of compounds or pharmaceutically acceptable acid addition salts thereof in the context of the present invention are any hydrates (hydrated forms) thereof.

Within the context of the present invention, a "ligand for the receptor GHS-R 1A" is understood to refer to any compound that has affinity to the receptor GHS-R 1A as measured by the method as described in Example 1 herein.

Within the context of the present invention, treatment is to be understood as treatment and/or prevention.

In a still further aspect, the invention relates to a pharmaceutical composition comprising, as an active ingredient, a compound as defined above or a pharmaceutically acceptable salt thereof together with a pharmaceutically acceptable carrier.

In a further aspect of the invention the present compounds may be administered in combination with further pharmacologically active substances, e.g., an antidiabetic agent or other pharmacologically active material, including other compounds for the treatment and/or prevention of insulin resistance and diseases wherein insulin resistance is the pathophysiological mechanism.

Furthermore, the compounds according to the invention may be administered in combination with other food intake-regulating agents.

A still further aspect of the present invention is a method of identifying candidate compounds that regulate food intake, characterized by screening out compounds that act as ligands for the receptor GHS-R 1A. This method for identifying candidate compounds comprises:

(a) contacting a growth hormone secretagogue receptor type 1A (GHS-R 1A), or a fragment thereof having GHS-R 1A ligand-binding activity, in the presence of increasing amounts of a compound of interest not known to have GHS-R 1A ligand-binding activity;

(b) measuring the binding of the known GHS-R 1A ligand to the GHS-R 1A receptor; and (c) determining the concentration of the compound of interest at which the binding of said ligand to said receptor is reduced to 50% of binding in the absence of said compound, wherein, if said concentration is about 500 nm or less, the compound is a candidate compound that regulates food intake.

A further aspect of the present invention relates to a compound identified by or identifiable by this method.

Pharmaceutical Composition

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, $19^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the choice of route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings, such as enteric coatings, or they can be formulated so as to provide controlled release of the active ingredient, such as sustained or prolonged release according to methods well known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions, as well as sterile powders to be reconstituted in sterile injectable solutions or dispersions prior to use. Depot injectable formulations are also contemplated as being within the scope of the present invention.

Other suitable administration forms include suppositories, sprays, ointments, creams, gels, inhalants, dermal patches, implants, etc.

A typical oral dosage of a compound employed according to the invention is in the range of from about 0.0001 to about 100 mg/kg body weight per day, preferably from about 0.001 to about 10 mg/kg body weight per day, and more preferably from about 0.01 to about 1 mg/kg body weight per day, administered in one or more doses, such as 1 to 3 doses.

The formulations may conveniently be presented in unit dosage form by methods known to those skilled in the art. A typical unit dosage form for oral administration one or more times per day, such as 1 to 3 times per day, may contain from about 0.05 to about 2000 mg, preferably from about 0.1 to about 500 mg, and more preferably from about 0.5 mg to about 200 mg of a compound employed according to the invention.

For parenteral routes, such as intravenous, intrathecal, intramuscular and similar routes of administration, doses are typically of the order of about half the dose employed for oral administration.

The compounds of this invention are generally utilized as the free substance or as a pharmaceutically acceptable salt thereof. One example is an acid addition salt of a compound having a free base functionality. When a compound of the invention contains a free base functionality, such salts are suitably prepared in a conventional manner by treating a solution or suspension of the free base form of the compound with, typically, one equivalent (chemical equivalent, i.e. acid-base equivalent) of a pharmaceutically acceptable acid, for example an inorganic or organic acid chosen among the representative examples thereof mentioned above. Physiologically acceptable salts of a compound with a hydroxy group include the anion of said compound in combination with a suitable cation, such as sodium or ammonium ion.

For parenteral administration, solutions of the present compounds in sterile aqueous solution, aqueous propylene glycol or sesame or peanut oil may be employed. Such aqueous solutions should be suitably buffered if necessary, and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water. Similarly, the carrier or diluent may include any sustained-release material known in the art, such as glyceryl monostearate or glyceryl distearate, alone or mixed with a wax. The pharmaceutical compositions formed by combining the compounds of the invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

If a solid carrier is used for oral administration, the preparation may be tabletted, placed in a hard gelatin capsule in powder or pellet form, or it can be in the form of a troche or lozenge. The amount of solid carrier will vary widely, but will usually be from about 25 mg to about 1 g. If a liquid carrier is used, the preparation may be in the form of a syrup, emulsion, soft gelatin capsule or sterile injectable liquid, such as an aqueous or non-aqueous liquid suspension or solution.

A typical tablet that may be prepared by conventional tabletting techniques may contain:

Core:

| | |
|---|---|
| Active compound (as free compound or salt thereof) | 5 mg |
| Colloidal silicon dioxide (Aerosil ™) | 1.5 mg |
| Cellulose, microcryst. (Avicel ™) | 70 mg |
| Modified cellulose gum (Ac-Di-Sol ™) | 7.5 mg |
| Magnesium stearate | q.s. |

Coating:

| | |
|---|---|
| Hydroxypropylmethylcellulose (HPMC) approx. | 9 mg |
| *Mywacett ™ 9-40 T approx. | 0.9 mg |

*Acylated monoglyceride used as plasticizer for film coating.

The compounds of the invention may be administered to a mammal, especially a human, in need thereof. Such mammals include also animals, both domestic animals, e.g., household pets, and non-domestic animals such as wildlife.

If desired, the pharmaceutical composition of the invention may comprise the compound of the invention in combination with further pharmacologically active substances such as those described in the foregoing.

The present invention is further illustrated by the following examples which, however, are not to be construed as limiting the scope of protection.

EXAMPLES

Example 1

Identification of Ligands for the Receptor GHS-R 1A

Transfection

Lipofectamine (Life Technologies, Rockville, Md., U.S.A.) was used for transfection of BHK cells with a GHS-R 1A expression vector (Howard, A. D. et al. (1996), Science 273, 974-977).

Receptor Binding Assay

Receptor binding was assayed as described in Hansen, B. S. et al (1999) Eur. J. Endocrinol. 141:180-189. Briefly, crude membranes from stably transfected BHK/GHS-R 1A cells were suspended at 0.5 mg protein/ml in homogenization buffer (25 mM Tris-base, 2.5 mM EDTA, 10 mM $MgCl_2$ and 30 µg/ml bacitracin). In a microtiter plate 10 µl membrane suspension was combined with either $^{35}$S-labelled MK0677 (see Example 4) (Amersham Pharmacia Biotech, Essex, UK) or 2-$^{3}$H-adenosine (Amersham) as well as binding buffer (2.5 mM Tris-base, 2.5 mM EDTA and 10 mM $MgCl_2$) to a total volume of 250 µl. Non-specific binding was determined by adding 10 µM MK0677 (see Example 4) or 10 µM adenosine to the assay. The assay was subsequently incubated at 30° C. for 60 minutes, followed by application of the samples to GF/B filters (Whatman, Kent, UK) which had been pretreated with 0.5% polyethylenimine for 60 minutes. The filters were subsequently washed in 0.9% NaCl and counted using an Optiphase™ 'HiSafe 3' counter (Wallac, Turku, Finland).

To test for compounds that can compete with binding of either $^{35}$S-MK0677 or $^{3}$H-adenosine to the GHS-R 1A, different concentrations (0.001 nmol/l to 10 µmol) of the compound were added to the incubation described above.

Specific binding was determined as the difference between total binding and non-specific binding (binding in the presence of 10 µM unlabelled ligand). Binding curves were generated using either the non-linear regression or hyperbolic fit feature of the GraphPad™ Prism software package (GraphPad, San Diego, Calif., U.S.A.).

Calcium Imaging

To test for agonism or antagonism of the compounds that can compete with the binding of the radiolabelled ligands in the above receptor assay, a functional assay based on stimulation of the release of $Ca^{++}$ via the GHS-R was developed.

GHSR-expressing cells were cultured in Lab-Tek™ chambered coverglasses (Nalge Nunc Int., Naperville, Ill., USA). Prior to the experiment, cells were loaded with the $Ca^{2+}$-sensitive dye, Fura2-AM (Molecular Probes Inc., Eugene, Oreg., U.S.A.), according to standard procedures. The chambers were placed on a temperature-regulated microscope stage and kept at 37° C. Fluorescence images were acquired using the MetaFluor™ software package (Universa) Imaging Corporation, West Chester, Pa., U.S.A.) together with a Zeiss Axiovert™ 100S inverted microscope (Carl Zeiss, Oberkochen, Germany) and a Princeton™ MicroMAX-5-1300Y CCD camera (Princeton instruments, Trenton, N.J., U.S.A.). The microscope was also equipped with a 530 nm±15 nm emission filter, a 500 nm dichroic mirror (Delta Lys & Optik, Lyngby, Denmark) and a filterwheel (LUDL electronic products, Hawthorne, N.Y., USA) harbouring 340 nm-±10 nm and 380 nm±10 nm excitation filters (Delta Lys & Optik). Images were acquired every 3 seconds. After acquisition of 12-14 images, the cells were stimulated with adenosine, MK0677 or other compounds. To test for antagonism the compounds were added together with either adenosine or MK0677. In each experiment the Fura2 ratio (ratio between the measured intensities of emission at 510 nm following excitation at 340 nm and at 380 nm, respectively) was followed in 50 cells. A normalized ratio was generated for each cell by dividing the Fura2 ratio at time t with the ratio at time zero. The data represented the average normalized Fura2 ratio for 50 cells in a typical experiment. All experiments were repeated at least 4 times (giving similar results).

Example 2

Identification of Adenosine as a Ligand for the Receptor GHS-R 1A

The methods of example 1 were used. Adenosine was found to be a potent ligand for the GHS-R 1A ($EC_{50}$~50 nM using the $Ca^{++}$ assay described above). Binding studies were performed to characterize the binding of adenosine to the GHS-R 1A, and a $K_D$ of 87±10 nM was determined.

Adenosine was, however, unable to stimulate GH secretion from rat pituitary cells (assay described e.g. in Hansen, B. S. et al (1999) Eur. J. Endocrinol. 141:180-189).

Example 3

Adenosine does not Stimulate Growth Hormone Release, but Stimulates Feeding

The effect on GH release was studied in Halothane anaesthetized male Wistar rats after intracerebroventricular (icy) and intravenous (iv) administration of adenosine and also in pentobarbital anaesthetized catheterized female Sprague Dawley (SD) rats after iv administration. Vehicle or adenosine was given to groups of rats (n=4-6) in the following doses: 10 µg/rat and 100 µg/rat icy dissolved in 5 µl saline, 1 mg/kg iv and also 10 mg/kg iv to the SD rats. Blood samples were obtained from anaesthetized animals before dosing, and either 10 min after dosing or by frequent blood sampling through a catheter up until 45 min after dosing. The plasma was analyzed for rat GH.

The effect on feeding was studied in conscious non-deprived male Wistar rats (n=7-10) after icy dosing of vehicle or adenosine (1 µg/rat and 10 µg/rat in 5 µl saline). Food intake was measured in feeding boxes with standard chow and water placed on balances connected to a computer. Changes in weight of chow and water were continuously registered. Food and water intake were measured for 3 hours after drug injection during early daytime, when food intake is normally at a very low level.

The results showed that adenosine did not stimulate GH release in any of the given doses, neither by the icy nor the iv route of administration.

With respect to the orexigenic effect of adenosine, there was no effect after 1 µg/rat, but food intake was significantly increased compared to the vehicle control group after injection of 10 µg/rat adenosine icy.

Example 4

Correlation Between GHS-R 1A Binding Affinity and the Effect on Food Intake

The compounds used were characterized by showing equipotency with respect to in vitro GH release from primary rat somatotrophs, although they displayed significantly different binding affinity to the GHS-R 1A.

The following compounds (structures shown below) were employed: NNC 26-1291, with a high binding affinity to the receptor similar to that of MK0677 ($K_i$=0.4±0.06 nM), NNC 26-1187 with an intermediate binding affinity ($K_i$=22.2±7 nM), and NN703 displaying a weak binding affinity ($K_i$=112±29 nM).

NN703 is described in WO 97/23508, and this compound, together with MK0677 (the latter also being denoted MK677), is also described in, e.g., Drug Discovery Today, vol. 4, No. 11, Nov. 1999, pp. 497-506. NNC 26-1291 and NNC 26-1187 are growth hormone secretagogues of a non-peptidyl nature and are described in WO 99/58501 and WO 00/26252, respectively.

The effect on feeding was tested after icy injections in non-deprived male Wistar rats. The compounds were dissolved in 5 µl saline and injected in the following doses: 10.0 µg per rat (NNC 26-1291) and 30.0 µg per rat (NN703 and NNC 26-1187).

Food intake was measured in feeding boxes, where standard chow and water were placed on balances and changes in weight continuously registered. Food and water intake was measured for 3 hours after drug injection in the beginning of the light part of the diurnal cycle, when food intake is normally at a very low level. All three compounds increased food intake. The effect of NN703 was moderate, with a food intake at about 3 grams, while NNC 26-1187 and particularly NNC 26-1291 showed stronger effects with food intakes at about 4-5 grams. For comparison, food intake in control animals is normally about 1 gram, and icy administration of 10 µg porcine neuropeptide Y (NPY), which has a strong effect on food intake, increases food consumption to about 8 grams in this model.

The compounds employed were as follows:

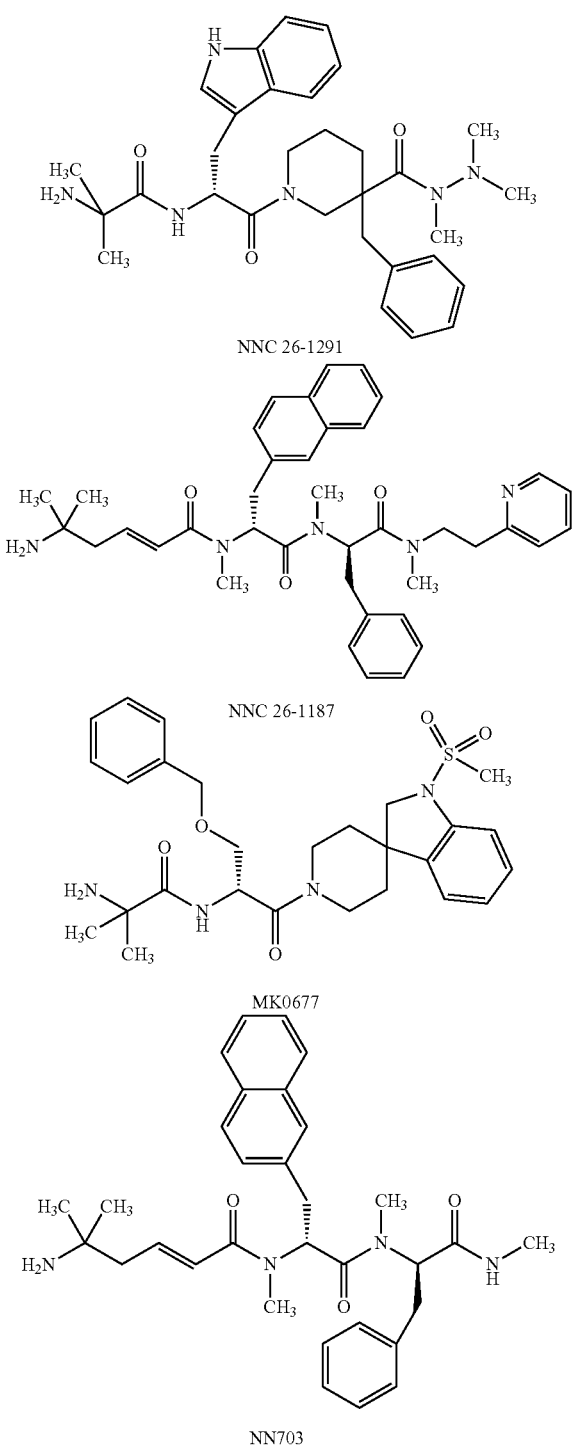

NNC 26-1291

NNC 26-1187

MK0677

NN703

Example 5

Ghrelin Stimulates Feeding, but not GH Release, after Icy Administration

Non-deprived male Wistar rats (n=6-10) were used for the study, dosed with vehicle or with ghrelin at 10 μg/rat icy dissolved in 5 μl saline. Food intake was measured in conscious animals, using feeding boxes. Food and water intake were measured for 3 hours after drug injection during early daytime, when food intake is normally at a very low level. GH release was measured in Halothane-anaesthetized animals from which blood samples were obtained, before dosing and 10 min after dosing, via the orbital plexus. The plasma was analyzed for rat GH.

Ghrelin administered in this manner (icy administration) produced a significant effect on feeding, compared to vehicle, but did not stimulate GH release. In contrast, it is known that ghrelin administration by the iv route causes stimulation of GH release.

What is claimed is:

1. A method for treating anorexia, comprising administering to a subject in need thereof a compound that is an agonist for the growth hormone secretagogue receptor type 1A (GHS-R 1A), wherein the agonist is NNC 26-1291 or a pharmaceutically acceptable salt thereof, in an amount effective for such treatment,

NNC 26-1291

2. The method of claim 1 wherein said compound is orally administered.

* * * * *